(12) United States Patent
Desmarais

(10) Patent No.: US 6,951,541 B2
(45) Date of Patent: Oct. 4, 2005

(54) MEDICAL IMAGING DEVICE WITH DIGITAL AUDIO CAPTURE CAPABILITY

(75) Inventor: Robert J. Desmarais, Litchfield, NH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 51 days.

(21) Appl. No.: 10/726,833

(22) Filed: Dec. 3, 2003

(65) Prior Publication Data

US 2004/0147842 A1 Jul. 29, 2004

Related U.S. Application Data

(60) Provisional application No. 60/435,239, filed on Dec. 20, 2002.

(51) Int. Cl.[7] .................................................. A61B 8/00
(52) U.S. Cl. ..................................................... 600/437
(58) Field of Search ................................ 600/407, 409, 600/437, 443, 447; 128/915, 916

(56) References Cited

U.S. PATENT DOCUMENTS

| | | | | |
|---|---|---|---|---|
| 4,924,387 A | * | 5/1990 | Jeppesen | 705/8 |
| 5,612,900 A | * | 3/1997 | Azadegan et al. | 709/247 |
| 5,799,310 A | * | 8/1998 | Anderson et al. | 707/102 |
| 5,971,923 A | * | 10/1999 | Finger | 600/437 |
| 6,231,508 B1 | | 5/2001 | Miller et al. | |
| 6,514,201 B1 | * | 2/2003 | Greenberg | 600/437 |
| 6,595,921 B1 | * | 7/2003 | Urbano et al. | 600/437 |

* cited by examiner

*Primary Examiner*—Francis J. Jaworski

(57) ABSTRACT

A medical imaging system including a sound recording sub-system that records, digitizes and time-stamps at least one channel of sound related to time domain images produced by the medical imaging system in accordance with a system clock signal. The sound recording sub-system indexes or synchronizes the at least one channel of sound to events in the plurality of time domain images, which are acquired, digitized and time-stamped in accordance with the system clock signal. The time-stamped, digitized at least one channel of sound is memory-stored.

26 Claims, 4 Drawing Sheets

MEDICAL IMAGING DEVICE WITH DIGITAL AUDIO CAPTURE CAPABILITY

CROSS REFERENCE TO RELATED APPLICATION

This application claims the benefit of application Ser. No. 60/435,239, filed on Dec. 20, 2002.

Many modern medical imaging devices produce time domain images, that is, the time (or relative time) at which such images are produced is diagnostically important. Such medical imaging devices typically capture a sequential series of images portraying movement of a structure under study. For example, known ultrasound systems capture sequential images which are output to a monitor and/or videotape using a video tape recorder. With the advent of digital ultrasound systems, it has become known to capture digital representations of still frame data and video, see, for example, U.S. Pat. No. 6,231,508.

It is also known to capture analog audio information related to the diagnostic procedure being performed by the medical imaging device. Once again, using an ultrasound system as an example, current systems capture voice annotation and Doppler audio on videotapes concurrent with the capture of images. Unfortunately, analog audio information is difficult to index and randomly search. Further, the analog audio data can only be associated with the videotape upon which it resides and due to the nature of videotape, only a single audio stream may be associated with any one video segment. Advanced manipulation of the stored analog information requires highly specialized video processing equipment. It is also difficult to transmit the analog audio information to a connected medical information system or other data processing device, which are inherently digital.

Connectivity between medical imaging devices and other information systems has been a concern since at least the early 1980's. Several standards for such interconnection have been developed. The most successful standard is DICOM (the Digital Imaging and Communications in Medicine standard), currently "managed" by NEMA (the National Electrical Manufactures Association). The DICOM standard encompasses all medical imaging devices including ultrasound, MRI, CAT, PET, X-ray and radiotherapy. DICOM provides for network image transfer, open media interchange and integration with healthcare information systems. To this end, the DICOM standard is organized with a central general standard and several specific standards for various medical imaging systems DICOM provides guidance on file formats and issues related to interconnectivity. For example, DICOM describes how to store and transmit ultrasound images, radiology images, ECG waveforms, etc. One of the file formats provided by DICOM is for basic voice audio. The basic voice audio 10D (Information Object Description) provides a basic mechanism for the transfer of audio data collected during an imaging session. The DICOM specification identifies dictation as the "typical use" and further specifies the sample frequency at 8 Khz (presumably at 16 bits). While, the DICOM audio standard is suitable for low information sounds, such as dictation, it is unsuitable for high information sounds, such as heart sounds, respiration, and Doppler audio. Further, DICOM does not provide a complete framework to index or synchronize such sounds against stored images.

The present invention recognizes a need to acquire audio signals, such as Doppler and voice annotation, etc. (audio data), and to time-stamp the audio data as it is converted to digital. For example, Doppler audio is time-stamped after conversion to digital and synchronized with time-stamped Doppler spectrum trace data which is itself converted to digital and time-stamped in the beamformer. Both such digital data may be memory-stored, and recalled and played synchronously based on the time-stamping. Voice annotation may also be input and synchronized to the Doppler spectrum trace information, imaging data, etc., and played back synchronously with such imaging information therefore. The timer used for time-stamping must available to all sub-systems which have an ability to acquire date, e.g., ECG, in order that all data within the system may be synchronized for archiving, playback, memory-storing, etc.

The present invention recognizes a need to acquire audio signals, such as Doppler and voice annotation (audio data), and to time-stamp the audio data as it is converted to digital, in order that the time-stamped, digitized audio data may be utilized synchronously with acquired ultrasound data, e.g., spectral, 2D, 3D, etc., which ultrasound data are time-stamped in the beamformer at acquisition/digital conversion.

The present invention also recognizes a need to memory-store audio data, such as voice, Doppler, etc., as it is acquired and digitized, such that it may used by the ultrasound system synchronously with acquired ultrasound data, e.g., spectral, 2D, 3D, B-mode, color lines, Doppler samples, etc.

The present invention also has recognizes a need for constantly acquiring audio during a medical examination, time stamping the audio data as it is digitized and arranged in an audio data stream, and directing the audio stream to any system location based on real-time events such as mode changes, probe changes, etc.

The present invention has further recognizes the need to playback audio data, acquired, digitized and time-stamped during a medical examination, independently, and/or synchronously.

The present invention has further recognized the need to automatically detect and record voice annotation (audio clip), which includes digitizing and time stamping the digitized voice annotation, and recognize the recorded and/or detected audio clip and converting the audio clip to text.

The present invention still further recognizes the need and/or the ability to create, store, index and synchronize captured, digitized and time-stamped digital audio information, whether existing in the DICOM format, and/or converting the digital audio information to the DICOM format.

An understanding of the present invention can be gained from the following detailed description of the invention, taken in conjunction with the accompanying drawings of which:

Reference will now be made in detail to the present invention, examples of which are illustrated in the accompanying drawings, wherein like reference numerals refer to like elements throughout.

Figure 1:
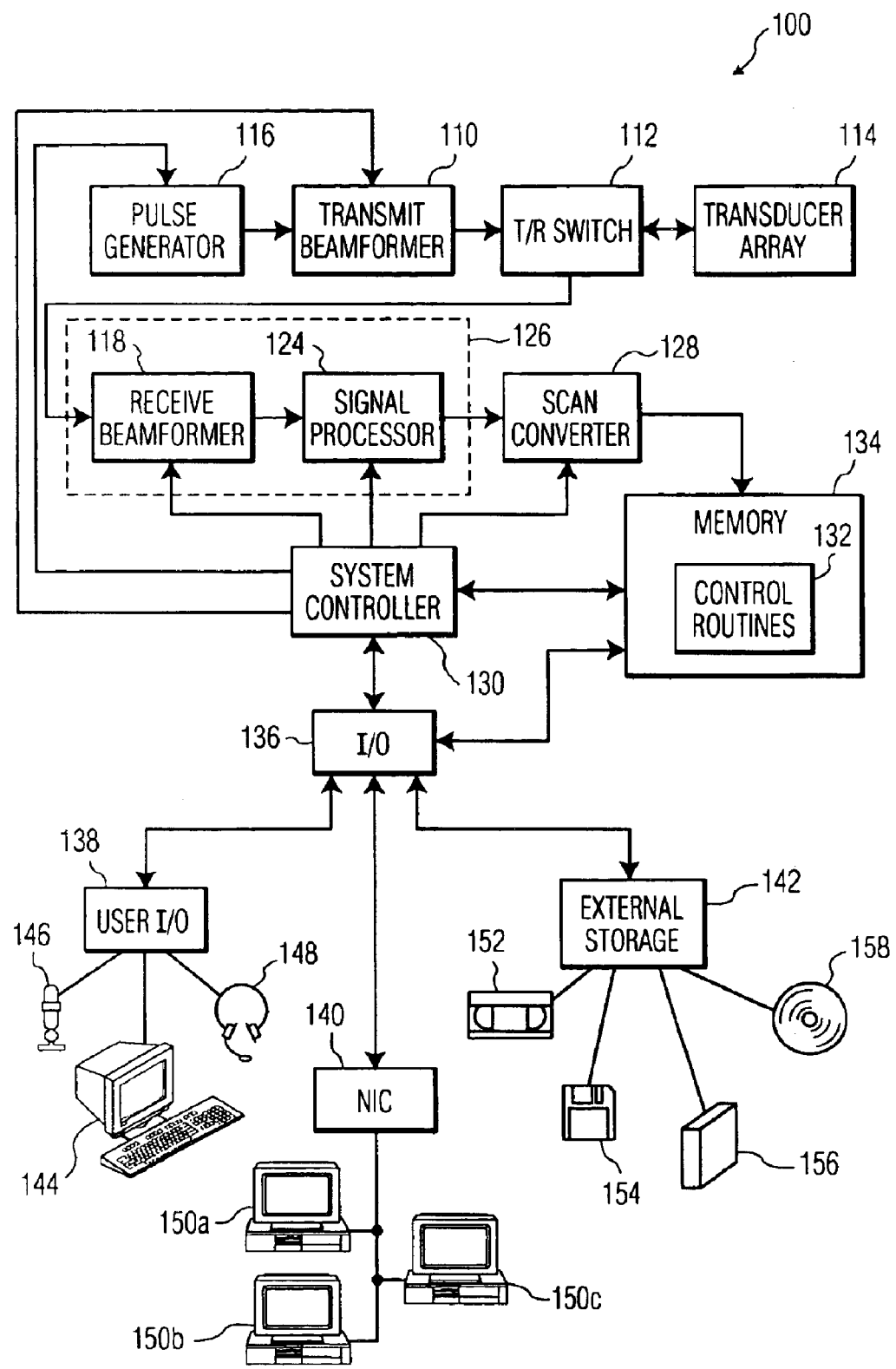
FIG. 1 is a block diagram of an ultrasound system in accordance with a preferred embodiment of the present invention.

The detailed description of preferred apparatus and methods that follow is presented in terms of routines and symbolic representations of operations of data bits within a memory, associated processors, and possibly networks, and network devices. These descriptions and representations are the means used by those skilled in the art effectively convey the substance of their work to others skilled in the art. A routine is here, and generally, conceived to be a self-consistent sequence of steps or actions leading to a desired result. Thus, the term "routine" is generally used to refer to a series of operations performed by a processor, be it a central processing unit of an ultrasound system, or a secondary processing unit of such an ultrasound system, and as such, encompasses such terms of art as "program," "objects," "functions," "subroutines," and "procedures."

In general, the sequence of steps in the routines requires physical manipulation of physical quantities. Usually, though not necessarily, these quantities take the form of electrical or magnetic signals capable of being stored, transferred, combined, compared or otherwise manipulated. Those of ordinary skill in the art conveniently refer to these signals as "bits", "values", "elements", "symbols", "characters", "images", "terms", "numbers", or the like. It should be recognized that these and similar terms are to be associated with the appropriate physical quantities and are merely convenient labels applied to these quantities.

In the present case, the routines and operations are machine operations to be performed in conjunction with human operators. Useful machines for performing the operations of the present invention include the ENVISOR ultrasound system, commonly owned by the owner of this invention, and other similar devices. In general, the present invention relates to method steps, software, and associated hardware including computer readable medium, configured to store and/or process electrical or other physical signals using the routines described herein to generate other desired physical signals.

The apparatus set forth in the present application is preferably specifically constructed for the required purpose, i.e. ultrasound imaging, but the methods described herein may be embodied on a general purpose computer or other network device selectively activated or reconfigured by a routine stored in the computer and interface with the necessary ultrasound imaging equipment. The procedures presented herein are not inherently related to any particular ultrasonic system, computer or other apparatus. In particular, various machines may be used with routines in accordance with the teachings herein, or it may prove more convenient to construct more specialized apparatus to perform the required method steps. In certain circumstances, when it is desirable that a piece of hardware possesses certain characteristics, these characteristics are described more fully in the following text. The required structures for a variety of these machines may appear in the description given below. Machines, which may perform the functions of the present invention, include those manufactured by such companies as PHILIPS MEDICAL SYSTEMS INTERNATIONAL, GE MEDICAL SYSTEMS, and SIEMANS MEDICAL SYSTEMS, as well as other manufacturers of ultrasound equipment.

With respect to the software described herein, those of ordinary skill in the art will recognize that there exist a variety of platforms and languages for creating software for performing the procedures outlined herein. Those of ordinary skill in the art also recognize that the choice of the exact platform and language is often dictated by the specifics of the actual system constructed, such that what may work for one type of system may not be efficient on another system.

FIG. 1 is a simplified block diagram of an ultrasound imaging system 100 in accordance with a preferred embodiment of the present invention. It will be appreciated by those of ordinary skill in the relevant arts that the ultrasound imaging system 100, as illustrated in FIG. 1, and the operation thereof as described hereinafter, is intended to be generally representative of medical imaging systems. Any particular system may differ significantly from that shown in FIG. 1, particularly in the details of construction and operation of such system. As such, the ultrasound imaging system 100 is to be regarded as illustrative and exemplary and not limiting as regards the invention described herein or the claims attached hereto.

The FIG. 1 ultrasound imaging system 100 shows a transmit beamformer 110 as coupled through a transmit/receive (T/R) switch 112 to a transducer array 114. Transducer array 114 includes an array of transducer elements. The T/R switch 112 typically has one switch element for each transducer element. The transmit beamformer 110 receives pulse sequences from a pulse generator 116. The transducer array 114, energized by the transmit beamformer 110, transmits ultrasound energy into a region of interest (ROI) in a patient's body and receives reflected ultrasound energy, or echoes, from various structures and organs within the patient's body. As is known in the art, by appropriately delaying the waveforms applied to each transducer element by the transmit beamformer 110, a focused ultrasound beam is transmitted.

The transducer array 114 is also coupled, through the T/R switch 112, to a receive beamformer 118. Ultrasound energy from a given point within the patient's body is received by the transducer elements at different times. The transducer elements convert the received ultrasound energy to transducer signals which may be amplified, individually delayed and then summed by the receive beamformer 118. Such operation provides a beamformer signal that represents the received ultrasound level along a desired receive line. The receive beamformer 118 may be a digital beamformer including an analog-to-digital converter for converting the transducer signals to digital values. As known in the art, the delays applied to the transducer signals may be varied during reception of ultrasound energy to effect dynamic focusing. The process is repeated for multiple scan lines to provide signals for generating an image of the region of interest in the patient's body. The receive beamformer 118 may, for example, be a digital beamformer of the type used in the SONOS 5500 ultrasound system manufactured and sold by the common owner hereof.

The beamformer signals are applied to a signal processor 124, which processes the beamformer signals for improved image quality. The signal processor may include processes such as harmonic processing. The receive beamformer 118 and the signal processor 124 constitute an ultrasound receiver 126. The output of the signal processor 124 is supplied to a scan converter 128, which converts sector scan or other scan pattern signals to conventional raster scan display signals. The time-stamping is preserved through any signal processing for use in image reconstruction. The output of the scan converter 128 is buffered for eventual display. Any acquired ultrasound data, e.g., B-mode, color lines, Doppler signals (e.g., CW), etc., is converted to digital and time-stamped in the beamformer.

A system controller 130 provides overall control of the system. The system controller 130 performs timing and control functions and typically includes a microprocessor operating under the control of control routines 132, stored in a memory 134. As will be discussed in detail below, the control routines 132, in addition to known control routines, include a variety of routines to create, store, index, and synchronize digitized audio information. The system controller 130 also utilizes the memory 134 to store intermediate values, including system variables describing the operation of the ultrasound imaging system 100, and to buffer various outputs, including the output of the scan converter 128.

An Input/Output unit 136 (hereinafter referred to as "I/O 136") controls a variety of input and output operations. For convenience, such operations have been logically organized into three groups: user I/O 138; network interface 140; and external storage 142. As known to those of ordinary skill in the art, the physical or logical organization of the I/O 136 may differ from that shown in FIG. 1 and will vary from system to system. FIG. 1 simply provides a convenient reference for explanatory purposes.

The user I/O group 138 provides an I/O for the user and may include, for example, one or more microphones 146 with associated A/D converter (not shown), a terminal 144 (including a display unit and a keyboard unit), and a headset 148 (with optional microphone). Other possibilities include speakers, a mouse, a trackball, a touch pad, and a touch screen. The ultrasound imaging system in accordance with the preferred embodiments of the present invention captures audio signals, converts the captured audio to digital and stores at least one channel of the digitized audio (discussed hereinbelow) via, for example, the microphones of the user I/O group 138.

The digitized audio is time-stamped in order that it may be synchronized with other ultrasound imaging information, e.g., a Doppler spectral trace. Of course the audio (data) information may take any form available from the various I/O described in the previous paragraph(s). That is, audio data may be Doppler audio, voice annotation, an imported audio clips, etc. The ENVISOR ultrasound system uses a 1 MHz clock (timer) which is provided by the token ring communication hardware as the time-stamp source. The 1 MHz clock is available to all ENVISOR subsystems. Time stamping based on a global system clock is the basis for synchronizing all subsystems during playback of digitized, time-stamped data acquired or stored in the sub-system, whether audio or ultrasound image data. Any verbal audio information may be translated to text, and the text accorded the same time stamp as the audio for text synchronization with the acquired ultrasound image data (time-stamped). The network interface 140 (e.g. a network interface card 140) facilitates networking with other devices, such a PC's 150a through 150b. Preferably, such communication takes place using the appropriate DICOM standards. The external storage group 142 may be utilized for more permanent and/or transportable storage of data. Examples of devices suitable for use as the suitable external storage 142 include: A video tape (analog or digital) unit 152; a floppy disk drivel 54; a ZIP drive 156; and a CD-RW drive 158 (CD-R and DVD-R). These may be the source of the audio information, and its manipulation in accordance with the inventive concepts herein.

Figure 2:
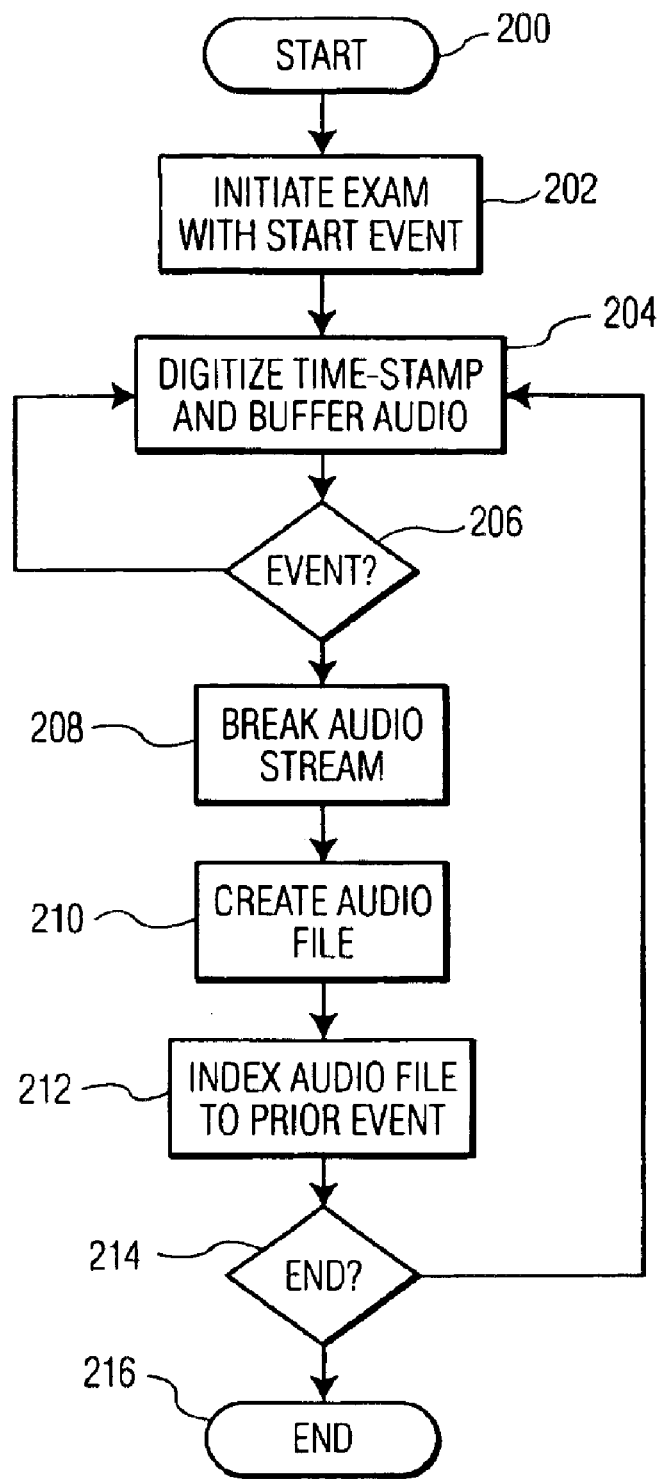
FIG. 2 is a flowchart of a method in accordance with a preferred embodiment of the present invention.

FIG. 2 is a flowchart of a method in accordance with a preferred embodiment of the present invention. In accordance with the preferred embodiment, the captured, digitized and time-stamped audio streams are split into a plurality of files based on events. In general, an event, as used herein, is a change in the operation of the imaging device upon which the present invention is being practiced, such as the ultrasound system 100 in FIG. 1, or just a time-triggered event. For example, a start of exam, end of exam, a mode change and probe changes would generate events. Events can also be based on user input preferably indicating a change in the Exam without a corresponding change in the mode or operation of the imaging device. Such a user input might be adjustments to obtain various views in known stress exams, or the injection of some imaging agent like contrast agent. The creation of multiple files facilitates the indexing of digitized audio clips to relevant patient data as described hereinbelow. Each event is time correlated, and the audio stream is time-stamped to indicate the time of the event occurrence so same audio stream may be used in the time synchronized operation contemplated and disclosed herein The method is started in step 200 and an exam is initiated with a start event in step 202. After the initiation of an exam in step 202, audio is digitized, time-stamped and buffered in step 204. Preferably, the captured, digitized audio is encoded at 22 to 44.1 KHz, and preferably at 44.1 KHz. The digitized data is preferably buffered in a format that is suitable for the creation of a file as taught herein, and may be provided with header data that associates the audio information contained in the file with the particular exam being conducted. An example of such header data is a serial number that is cross indexed with an identification table, time and date stamps, patient id, etc. The present invention provides that such header data may be supplied later with the actual creation of a file, to be described in greater detail below.

In accordance with the present invention, several types of audio information are individually digitized, time-stamped and buffered, preferably as individual channels. Specifically, ECG, audio inputs from external sources, heart sounds, respiration audio data, Doppler audio data, and voice annotation channels may be digitized and time-stamped in separate or combined streams. Digitization may be performed by dedicated hardware, or a combination of hardware and software, as part of the user I/O group 138, such as any number of commercially available digitizers. Any controller available may implement the time stamping for that purpose. As previously mentioned, acquired ultrasound data are digitized and time-stamped in the beamformer for use synchronized operations within the system. A preferred embodiment of the invention is embodied in ENVISOR, wherein a 1 MHz system clock accessible in all sub-systems via ENVISOR's token ring communication hardware provides the time-stamp clock signal. All data acquired/input to ENVISOR is time-stamped with the 1 MHz clock.

Next, step 206 includes performing a check or inquiry to determine if an event has occurred. As noted above, events can be automatically generated or user generated. Until a new event occurs the routine simply loops between steps 204 and 206 with the various audio channels being continually digitized and buffered. Upon the occurrence of an event, the routine goes to step 208, whereby the various audio streams are separated (broken). In general, unless the event is an end exam event, the input on the various audio channels is continually buffered. Some indication must be provided, however, which indicates the time of the event in the audio stream, whether the time is detected at the event, or in the data input defining the event. Some examples of such indications include: changing the buffer in which the digitized data is directed, insertion of "other data" into the digitized audio stream, indexing the digital audio file, a flag or other indicia that an event for post capture splitting of the audio stream has occurred, etc.

In accordance with the preferred embodiments of the present invention, an event causes the creation of a separate digitized audio file associated with the current or prior event, time stamped for synchronized with th event for any of the various purposes contemplated herein. Thus, most exams will result in the creation of a plurality of individual digitized audio files, the number of which is dependent upon the number of events that occur during the exam. As is known to those of ordinary skill in the art, the creation of the separate file can be performed at the time of an event or delayed (with appropriate recording of the time of the event) until anytime post-capture. The exemplary method shown in FIG. 2 illustrates the creation of a new file upon the occurrence of an event in step 210. In accordance with the preferred embodiment of the present invention, the created file is compatible with the wave format (.WAV). Wave files are a part of a file interchange format, called RIFF, created by Microsoft. The format basically is composed of a collection of data chunks as shown in Table 2. Each chunk has a 32-bit Id field, followed by a 32-bit chunk length, followed by the chunk data. Note that values are in Intel form (i.e.: big-endian notation).

TABLE 1

| Offset | Description |
| --- | --- |
| 0x00 | chunk id 'RIFF' |
| 0x04 | chunk size (32-bits) |
| 0x08 | wave chunk id 'WAVE' |
| 0x0C | format chunk id 'fmt' |
| 0x10 | format chunk size (32-bits) |
| 0x14 | format tag (currently pcm) |
| 0x16 | number of channels 1 = mono, 2 = stereo |
| 0x18 | sample rate in hz |
| 0x1C | average bytes per second |
| 0x20 | number of bytes per sample 1 = 8-bit mono; 2 = 8-bit stereo or 16-bit mono; and 4 = 16-bit stereo |
| 0x22 | number of bits in a sample |
| 0x24 | data chunk id 'data' |
| 0x28 | length of data chunk (32-bits) - does not include chunk Id or the length byte |
| 0x2C | Sample data |

For samples with more than 1 channel, channel 0 data will start and be followed by channel 1 for a given sample; then the next sample will follow. For example, in 8-bit stereo, the samples could be sample0left, sample0right, sample1left, sample1right, etc . . .

Of course other formats, such as MPEG2 layer 3 (.mp3), raw audio (.ra), and REAL AUDIO may be utilized. The reason for the preference for the .wav format is the ready availability of tools, the relative loss-less nature of the encoding, as well as its inherent support for high (44.1 KHz) sampling rates.

In step 212, each audio file is indexed to the prior event. Alternatively, the audio can be indexed to the current event. In either case, there are a variety of possible ways to index each digitized event-created audio file, the most preferable being time stamping. A master table can be created and maintained that indexes the various events against the various audio files, for example:

TABLE 2

| Exam | Patient | Event | Sound File | Type | Image Index |
| --- | --- | --- | --- | --- | --- |
| 5.8.01A | 001234 | Start | st001.wav | Dictation | 0:00:01 |
| 5.8.01A | 001234 | Start | st002.wav | Doppler | 0:00:01 |
| 5.8.01A | 001234 | Start | st003.wav | Heart | 0:00:01 |
| 5.8.01A | 001234 | Start | st004.wav | EKG | 0:00:01 |
| 5.8.01A | 001234 | Event001 | E01001.wav | Dictation | 0:07:34 |
| 5.8.01A | 001234 | Event001 | E01002.wav | Doppler | 0:07:34 |
| 5.8.01A | 001234 | Event001 | E01003.wav | Heart | 0:07:34 |
| 5.8.01A | 001234 | Event001 | E01004.wav | EKG | 0:07:34 |

Once the various audio files have been created and indexed (e.g., time-stamped), a check is made by the FIG. 2 method to determine if the current event was an End event. If the current event was an End event, the routine ends in step 216, otherwise the routine returns to step 204.

Once the various audio files have been created, they can be used in a variety of manners. The audio clips can be transmitted, preferably as some variant of a DICOM data element, to an imaging database system. For example, the digitized audio file may be transferred to one of the PCs 150a through 150c provided as part of the ultrasound imaging system 100 set forth in FIG. 1. Once in the imaging database system, the digitized audio files may be associated with multiple instances of clinical information in a many-to-many relationship. This allows the retrieval and playback of the digitized audio files based on both the exam data, including the imaging files, and clinical information, including patient identification, all based on the indexing or time stamping. As the preferred relationship is a many-to-many relationship, multiple audio files can be indexed to a single piece of clinical data, and vice-versa, allowing the operator to navigate to and play desired audio streams easily. Further, once a file is selected for playback, all indexed pieces of clinical data (or indications thereof) can be displayed allowing navigation based on the audio.

Figure 3:
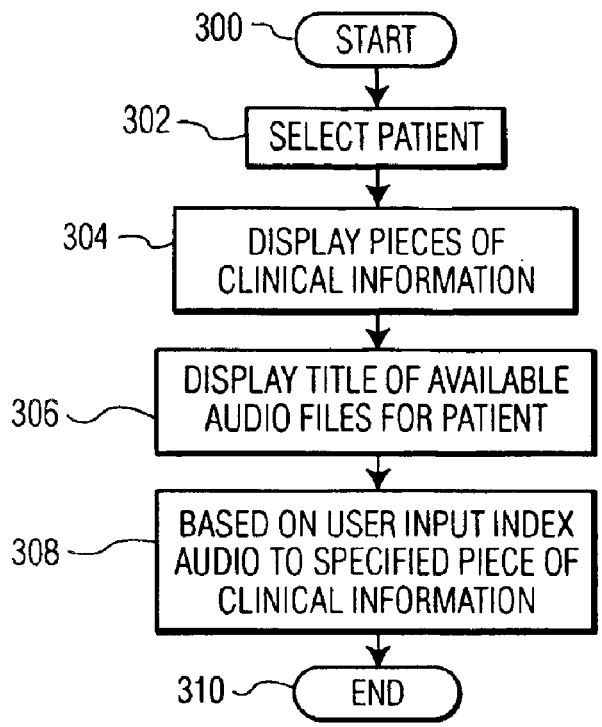
FIG. 3 is a flowchart of a method in accordance with the preferred embodiment of the present invention.

FIG. 3 is a flowchart of a method in accordance with the preferred embodiment of the present invention. Specifically, FIG. 3 shows a routine for the manual association of pieces of clinical information with audio files in a clinical information system, such as the ENCONCERT system sold by the common owner hereof. Those of ordinary skill in the art are able to modify any existing clinical information system to add the functions described in the routine shown in FIG. 3. The routine starts in step 300. In step 302, the user selects a patient on a terminal such as one of the PCs 150a through 150c of the ultrasound system in FIG. 1. Thereafter, in step 304, the routine displays pieces of clinical information indexed to the selected patient. Any imaging data for display may be displayed with the time-correlated audio stream associated therewith in accordance with the inventive concepts herein.

Next, in step 306, the routine displays the title (and optional description) of related audio files. This can be accomplished in several ways, for example, the user can be asked to determine which files are related to the patient by selecting a source, indexed for example by patient and/or date of exam as in TABLE 2 or the time-stamp. A routine can be constructed to perform an automated search by consulting an appropriately maintained index.

Thereafter, in step 308, the user provides input to index the listed audio files to specified pieces of clinical information. For example, audio files related to heart sounds can be related to an entry describing a certain heart condition readily identifiable by the heart sound. An entry describing a patients ECG can be linked to the ECG sounds. The routine ends in step 310. Those of ordinary skill in the art will recognize that routines can be constructed to automate much, if not all, indexing. Further, with appropriate communication between the imaging system and any relevant medical information system, the indexing operation can be performed contemporaneously with the exam, either manually or automatically.

Figure 4:
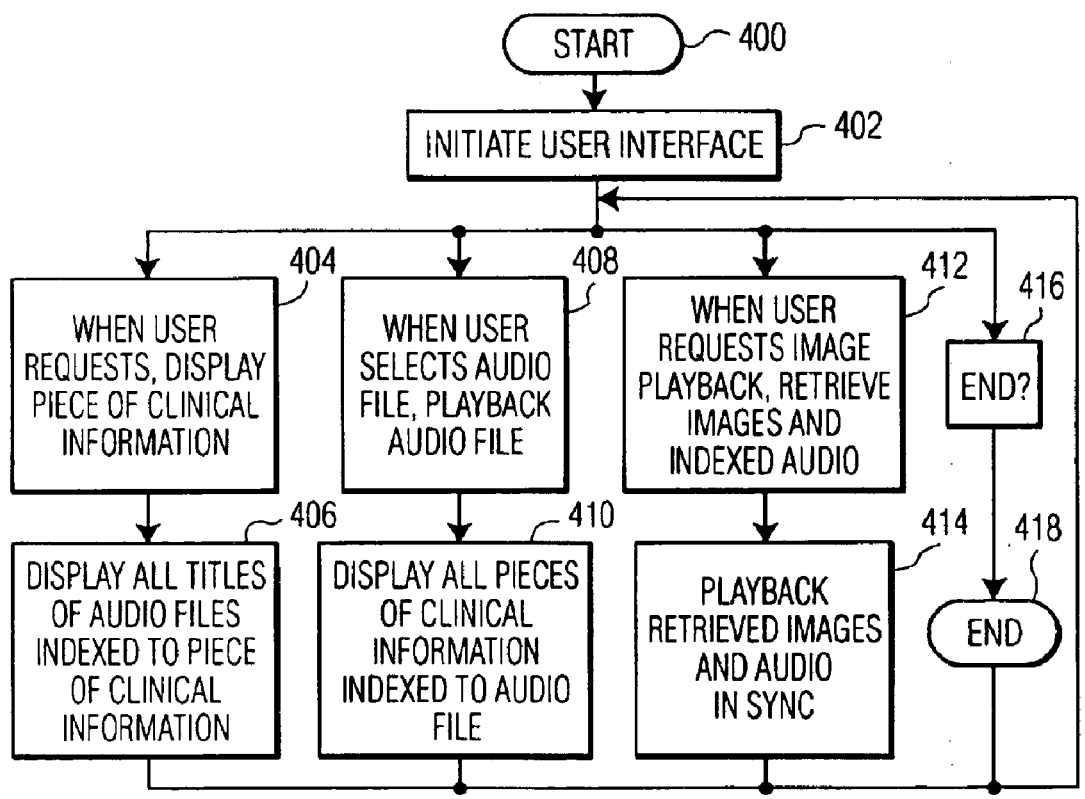
FIG. 4 is a flowchart of a method in accordance with the preferred embodiment of the present invention.
Figure 5:
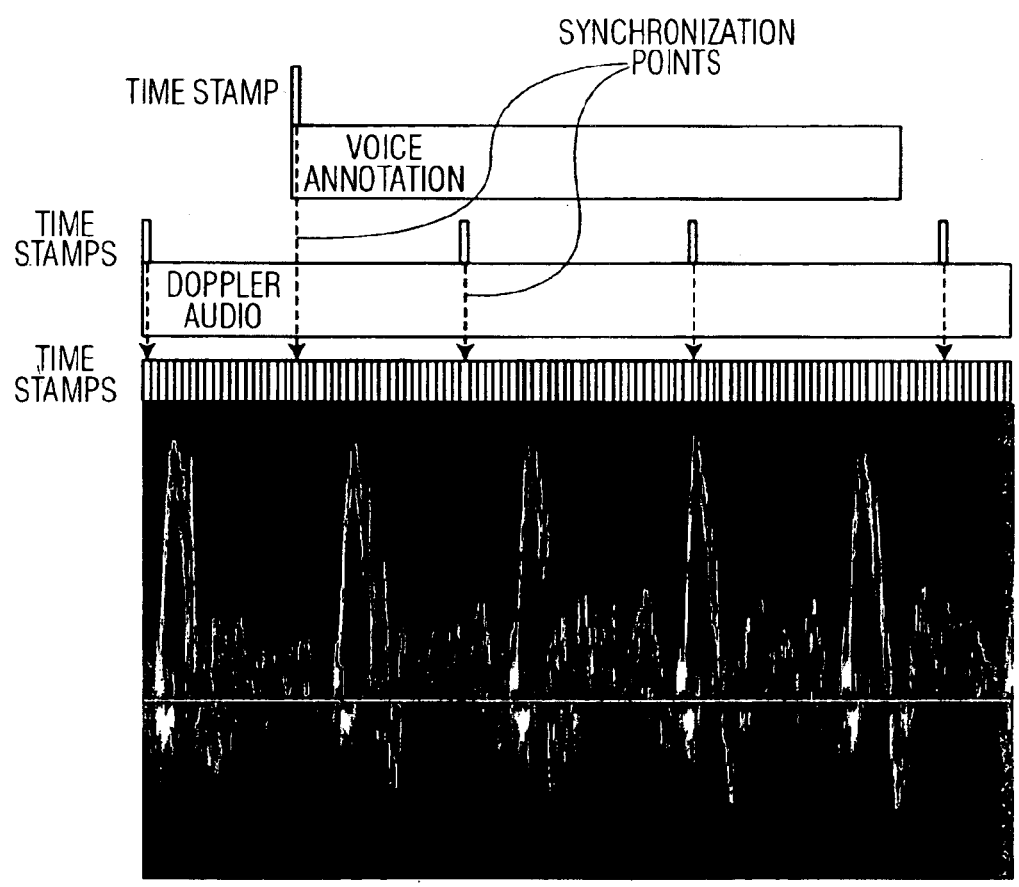
FIG. 5 is a loop of a Doppler trace.

FIG. 4 is a flow chart of a method in accordance with the preferred embodiment of the present invention. Specifically, FIG. 4 shows a routine for the retrieval and playback of digitized audio files in a clinical information system, e.g., the commonly owned ENCONCERT system. The routine starts in step 400 and in step 402 a user interface is polled (initiated). The details of the user interface are not necessary for an understanding of the present invention. Rather, the interface is dictated by the specific clinical information system being utilized.

The next action depends upon the nature of received user initiated events ("user requests"). If the user requests the display of a piece of clinical information, the requested information is displayed in step 404. Thereafter, in step 406 the titles of all digitized audio files are indexed to the piece of clinical information are displayed for selection.

If the user requests the playback of a digitized audio file associated with the displayed audio title, the playback is commenced in step 408. Thereafter, in step 410, indications of the various pieces of clinical information that are indexed to the digitized audio file being played are displayed for selection.

When the user requests the playback of stored image sequences, the requested image files are retrieved along with digitized audio files indexed thereto. Next, in step 414, the image files are played in sync with the playback of the indexed, digitized audio files. All annotation or Doppler audio is played synchronously with the display of the image files As with known event driven systems, the system continues to respond to user requests until a shut down request is received in step 416, and the routine is consequently ended in step 418.

The three user requests described above provide a foundation for the construction of a system that takes advantage of audio files obtained and indexed in accordance with the present invention. There are a variety of other user requests that could be implemented in a system constructed in accordance with the present invention. For example, a user request could be formulated to digitally process a requested digitized audio file to, for example reduce noise therein, characterize and/or chart the level of sound recorded in the digital audio file, etc. As another example, a user request could be formulated that submits a requested digitized audio file (preferably a dictation file) to a voice-to-text routine.

Although a few examples of the present invention have been shown and described, it would be appreciated by those skilled in the art that changes might be made in these embodiments without departing from the principles and spirit of the invention, the scope of which is defined in the claims and their equivalents.

What is claimed is:

1. A medical imaging system, comprising:
    a system clock for generating a synchronization signal;
    a medical imaging sub-system that procures a plurality of time domain images of internal structure within a patient during a medical diagnostic procedure being performed on the patient and digitally converts the time domain images to digitized time domain image data; and
    a sound recording sub-system that records, digitizes and time-stamps at least one channel of sound related to the time domain images in accordance with the synchronization signal, the sound recording sub-system indexing the at least one channel of sound to at least three events related to the medical diagnostic procedure or to operation of the imaging sub-system to split the at least one channel of sound, based on the events, into a plurality of digitized time-stamped audio data files which are synchronized with the time-stamped, digitized time domain image data.

2. The medical imaging system as set forth in claim 1, further comprising a memory for digitally storing the indexed, time-stamped audio data files.

3. The medical imaging system as set forth in claim 2, further comprising a playback sub-system that accesses and displays reconstructed images from the digitized time domain image data and synchronizes the playing of the time-stamped audio data files, based on the events.

4. The medical imaging system as set forth in claim 3, wherein the sound recording sub-system indexes the at least one channel of sound with a plurality of pieces of clinical information related to the patient and wherein the playback sub-system enables the access and playback of multiple pieces of audio information from the at least one channel of sound on a display showing a piece of clinical information related to the patient.

5. The medical imaging system as set forth in claim 1, wherein the imaging sub-system comprises an ultrasound imaging system.

6. The medical imaging system as set forth in claim 5, wherein the at least one channel of sound is digitized at 22 to 44.1 KHz and encoded in a wave compatible format.

7. The medical imaging system as set forth in claim 5, wherein the at least one channel of sound is comprises a Doppler audio signal.

8. The medical imaging system as set forth in claim 5, wherein the at least one channel of sound comprises ECG sounds.

9. The medical imaging system as set forth in claim 5, wherein the at least one channel of sound comprises heart sounds.

10. The medical imaging system as set forth in claim 5, wherein the at least one channel of sound comprises respiration sounds.

11. The medical imaging system as set forth in claim 1, wherein the at least one channel of sound includes dictation audio and wherein the medical imaging system further comprises:
    a voice recognition subsystem that translates the dictation audio into typed text, and wherein said typed text is time-stamped for indexing and synchronization.

12. The medical imaging system as set forth in claim 1, wherein the sound recording sub-system indexes the at least one channel of sound with clinical information related to the patient.

13. The medical imaging system as set forth in claim 1, wherein the sound recording sub-system indexes the at least one channel of sound with a plurality of pieces of clinical information related to the patient.

14. The medical imaging system as set forth in claim 1, wherein an event includes: start of exam; change of imaging mode; change of probe; user actuation of a control device; and end of exam.

15. A method for obtaining imaging and sound information during a medical diagnostic procedure, the method comprising:
    performing the medical diagnostic procedure on a patient:
    procuring a plurality of time domain images of internal structure within the patient during the medical diagnostic procedure;
    digitizing the time-domain images, and time-stamping the digitized time domain images with a system synchronization signal;
    receiving at least one channel of sound related to the time domain images;
    digitizing and time-stamping the least one channel of sound with the system synchronization signal; and
    indexing the at least one channel of sound to at least three events related to the medical diagnostic procedure or to the procurement of the plurality of time domain images to split the at least one channel of sound, based on the events, into a plurality of digitized time-stamped audio data files which are synchronized with the digitized time-stamped time domain images.

16. The method as set forth in claim 15, further comprising the steps of:
displaying the plurality of digitized time domain images; and
playing the audio data files based on the events synchronized with the display of the plurality of time domain images.

17. The method as set forth in claim 16, further comprising the step of indexing the audio clip data files with clinical information related to the patient based on time-stamping in accordance with the system synchronization signal.

18. The method as set forth in claim 16, further comprising the steps of:
indexing the audio data files with a plurality of pieces of clinical information related to the patient based on time-stamping in accordance with the system synchronization signal;
displaying a piece of clinical information related to the patient; and
enabling the access and playback of the audio data files indexed to the piece of clinical information being displayed upon request by a user.

19. The method as set forth in claim 15, wherein the step of procuring a plurality of time domain images of a patient comprises procuring a plurality of ultrasound images.

20. The method as set forth in claim 15, wherein the step of digitizing and time-stamping comprises digitizing the at least one channel of sound at 22 to 44.1 KHz, and wherein the computer readable file is wave compatible.

21. The method as set forth in claim 15, wherein the at least one channel of sound comprises a Doppler audio signal.

22. The method as set forth in claim 15, wherein the at least one channel of sound comprises ECG sounds.

23. The method as set forth in claim 15, wherein the at least one channel of sound comprises heart sounds.

24. The method as set forth in claim 15, wherein the at least one channel of sound comprises respiration sounds.

25. The method as set forth in claim 15, wherein the at least one channel of sound includes dictation audio and wherein the method further comprises the step of:
translating the dictation audio into a computer readable file having character data which is time-stamped in accordance with the system synchronization signal.

26. The method as set forth in claim 16, further comprising the step of indexing the audio data files with a plurality of pieces of clinical information related to the patient based on time-stamping in accordance with the system synchronization signal.

* * * * *